United States Patent [19]

Garsky

[11] 4,183,848
[45] Jan. 15, 1980

[54] ANALGESIC POLYPEPTIDE
[75] Inventor: Victor M. Garsky, Radnor, Pa.
[73] Assignee: American Home Products Corporation, New York, N.Y.
[21] Appl. No.: 838,688
[22] Filed: Oct. 3, 1977
[51] Int. Cl.² .................... C07C 103/52; A61K 37/00
[52] U.S. Cl. ............................... 260/112.5 R; 424/177
[58] Field of Search .................. 260/112.5 R; 424/177
[56] References Cited
PUBLICATIONS H. E. Blerch et al., Biochem. & Biophys. Res. Commun., 74, 1977, pp. 592–598.
L. Terenius et al., Biochem. & Biophys. Res. Commun., 71, 1976, pp. 175–179.
J. Hughes et al. Nature, 258, 1975, pp. 577–579.
D. H. Coy et al., Biochem. & Biophys. Res. Commun., 73, 1976, pp. 632–638.

C. B. Pert et al., Opiates and Endogenous Oipiod Peptides, 1976, pp. 79–86.

*Primary Examiner*—Delbert R. Phillips
*Attorney, Agent, or Firm*—Richard K. Jackson

[57] ABSTRACT

The polypeptide of the formula:

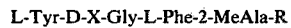

L-Tyr-D-X-Gly-L-Phe-2-MeAla-R in which
X is alanyl, methionyl or seryl
and
R is —OH, —NH$_2$ or -NHC$_n$H$_{2n+1}$ where n is 1,2,3 or 4 or a pharmaceutically acceptable salt thereof, exert an analgesic effect in warm-blooded animals when peripherally administered.

6 Claims, No Drawings

ANALGESIC POLYPEPTIDE

BACKGROUND OF THE INVENTION

Enkephalin, a natural opiate receptor agonist in the brain, has been identified [see Hughes et al., Nature, 258, 577(1975)] as a mixture of two pentapeptides: H-Tyr-Gly-Gly-Phe-Met-OH (methionine-enkephalin) and H-Tyr-Gly-Gly-Phe-Leu-OH (leucine-enkephalin). Both peptides mimic the ability of morphine to block electrically evoked contractions of mouse vas deferens and guinea pig ileum, and both inhibit the sterospecific receptor binding of the opiate antagonist 3H-naloxone in brain homogenates.

It has been proposed that enkephalin receptors may be sites at which morphine-like drugs exert their analgesic activities, and that enkephalin may be the modulator or transmittor in brain systems for pain suppression or analgesia. It has been reproted that methionine-enkephalin and leucine-enkephalin, when administered by injection in the brain ventricle in rats, induce a profound analgesia that is fully reversible by naloxone. [See Beluzzi et al., Nature, 260, 625(1976)]. The enkephalins are inactive when administered peripherally, however, and it is believed that the enkephalins are rapidly destroyed by blood enzymes and/or are poorly transported across the blood-brain barrier.

The amino acid sequence of methionine-enkephalin is identical to that of the N-terminal portion of the C-fragment ($\beta$-endorphin or $\alpha$-LPH[61–91]) of the peptide $\beta$-lipotropin, which is found in large concentrations in the pituitary and in much lower concentrations in the brain. Other naturally-occuring fragments of $\beta$-lipotropin are known, for example: $\alpha$-endorphin ($\beta$-LPH[61–76]) and $\gamma$-endorphin ($\beta$-LPH[61–77]). Both $\beta$-lipotropin and the endorphins show morphine-like properties in various test systems, and it has been suggested that methionine-enkephalin is a breakdown product of the large opiate-like peptides. Enkephalin, its relationship to $\beta$-lipotropin and the endorphins, and the pharmacological properties thereof, are reviewed in an article by Iversen et al., Nature, 262, 738(1976). Recent developments are also described in detail in the "Proceedings of the International Narcotics Research Club Meeting, Abderdeen, U.K., July 19–22, 1976," published in *OPIATES AND ENDOGENOUS OPIOID PEPTIDES*, North Holland Publishing Company, Amsterdam, 1976.

Various structural variations of methionine-enkephalin and leucine-enkephalin are described in the literature. For example, the pentapeptide H-Tyr-Gly-Gly-Phe-Thr-OH, wherein the fifth amino acid residue (methionine or leucine) is replaced by threonine, is described by Chang et al., Life Sciences, 18, 1473 (1976). Similarly, a long acting synthetic pentapeptide, Tyr-D-Ala-Gly-Phe-Met-amide is described in Pert et al., Science, 194, 330 (1976); which compound, like the natural enkephalins, is inactive when administered peripherally. Baxter et al., British Journal of Pharmacology, Mar. 2, 1977, pages 455P–456P and 523P report activity in the compound Tyr-D-Ala-Gly-Phe-D-Leu when administered intracerebroventricularly.

DESCRIPTION OF THE INVENTION

In accordance with this invention, there is provided a group of polypeptides of the formula:

Tyr-D-X-Gly-Phe-2-MeAla-R        I in which
X is alanyl, methionyl or seryl
and
R is —OH, —NH$_2$ or —NHC$_n$H$_{2n+1}$ where n is 1, 2, 3, or 4
or a pharmaceutically acceptable salt thereof.

All chiral amino acid residues in formula I and throughout this disclosure are in the natural or L-configuration unless otherwise indicated.

The preferred compounds are those of formula II:

Tyr-D-Ala-Gly-Phe-2-MeAla-R        II where R is —NH$_2$ or —NHC$_n$H$_{2n+1}$ and n is 1, 2, 3 or 4, or a pharmaceutically acceptable acid addition salt thereof.

The pharmaceutically acceptable salts of the polypeptides of this invention are acid addition salts of the free base in which the acid may be either organic or inorganic, as for example, hydrochloric, phosphoric, maleic, acetic, citric, succinic, malic, and similar acids. Likewise, salts of the free peptidic acid are embraced by the expression "pharmaceutically acceptable salts", and include the sodium, potassium, ammonium, and lower alkylamine salts. The salts are prepared and isolated by conventional methods.

The analgesic polypeptides of this invention are prepared by typical solid phase procedures employing either a benzhydrylamine polystyrene based resin for the production of the C-terminal amides or a chloromethylated or hydroxy methylated divinyl benzene crosslinked polystyrene resin for production of the C-terminal carboxylic acid or lower alkylamides. The polypeptide is removed from the resin support with HF and purified by gel filtration.

The analgesic activity of the polypeptides of this invention was demonstrated by the method of D-Amour and Smith, J. Pharmacol. Exp. Ther., 72, 74 (1941). The representative polypeptide of this invention Tyr-D-Ala-Gly-Phe-2-MeAla-NH$_2$, gave the following results in the reference standard rat tail flick test:

| Dose | Response No. showing analgesia/No. tested | | |
|---|---|---|---|
| Intravenous milligram/kilogram | minutes after administration | | |
| | 15 | 30 | 60 |
| 5.0 | 5/5 | 4/5 | 2/5 |
| 2.5 | 5/6 | 5/6 | 2/6 |
| 1.0 | 6/6 | 4/6 | 3/6 |
| .5 | 0/6 | 1/6 | 1/6 |
| Subcutaneous milligram/kilogram | minutes after administration | | |
| | 30 | 60 | 90 | 120 |
| 10.0 | 6/6 | 5/6 | 2/6 | 1/6 |
| 5.0 | 3/6 | 1/6 | 2/6 | 0/6 |

The test results demonstrate that the compounds of this invention induce analgesia upon administration of a single intravenous injection of about 1.0 milligrams per kilogram or more. For practical purposes, it is contemplated, based upon the preceding tesy results, that an intravenous dose of from about 1.0 to about 20 milligrams per kilogram in single or plural doses is the appropriate dosage to achieve that degree of analgesia desired for various applications. By subcutaneous administration, a dosage of about 5.0 milligrams per kilogram or more, produce the desired effect. The exact dose to be employed will, of course, vary somewhat with the specific compound employed, the patient and the degree of analgesia desired. The determination of a precise dose for production of a desired effect is readily determined empirically by the physician.

The following examples illustrate the preparation of the polypeptides of the invention.

EXAMPLE I

L-Tyrosyl-D-Alanylglycyl-L-Phenylalanyl-2-Methylalaninamide acetate

To a 200 ml. reaction vessel was added 10.0 g. of benzhydrylamine resin (9 m moles free amine content). The resin was then treated in the following manner:
1. methylene chloride (three times).
2. 5 minute prewash with 30% trifluoroacetic acid-methylene chloride (v/v) containing 0.5% dithioerythritol.
3. 25 minute treatment with the above described trifluoroacetic acid.
4. methylene chloride (three times).
5. 10 minute treatment with triethylamine-dimethylformamide (v/v).
6. dimethylformamide (three times).
7. methylene chloride (three times).

A contact time of 2 minutes is allowed for each wash unless otherwise indicated.

The resin is gently stirred with t-Boc-2-methylalanine and 1-hydroxybenzotriazole (HOBT) in 50% methylene chloride-dimethylformamide (9.14 g., 45 m moles t-Boc-2-MeAla and 7.66 g., 50 m moles HOBT). Following the addition of the above reagents the mixture was treated with 7.92 ml. of diisopropylcarbodiimide (the DIC was added in two equal portions over 30 minutes). After stirring overnight the peptide-resin was washed successively with dimethylformamide (twice), 12% triethylamine-dimethylformamide (once) and methylene chloride (thrice). To test for completeness of reaction the peptide-resin was subjected to a ninhydrin color test following the procedure of E. Kaiser et al., Analytical Chemistry 34, 595, (1970).

The deprotection of the attached amino acid was carried out as described in steps (2) through (7) above.

The following amino acid residues were then introduced consecutively: t-Boc-L-phenylalanine (7.0 g., 26 m moles, 3.6 g., 24 m moles HOBT and 4.2 ml., 26 m moles DIC), t-Boc-glycine (4.6 g., 26 m moles, 3.6 g HOBT and 4.2 ml. DIC), t-Boc-D-alanine (5.0 g., 26 m moles, 3.6 g. HOBT and 4.2 ml. DIC), t-Boc-O-benzyl-L-tyrosine (9.8 g., 26 m moles, 3.6 g. HOBT and 4.2 ml. DIC). The washed pentapeptide resin was dried in vacuo to yield 14.5 g.

The above described pentapeptide resin (14.5 g) was treated in vacuo with anhydrous liquid hydrogen fluoride (100 ml.) and anisole (10 ml.) at 0° for 1 hour. The hydrogen fluoride and anisole were removed under reduced pressure and the residue suspended in 2 N acetic acid, filtered and the filtrate lyophilized to yield the above title product, 1.5 g.

EXAMPLE 2

Purification and Characterization of L-tyrosyl-D-alanylglycyl-L-phenylalanyl-2-methylalaninamide, acetate The above titled crude product was purified as follows: 1.5 g. of material is dissolved in a minimum amount of 2 N acetic acid and applied to a column (2.5×200 cm) of Sephadex G-10 in 2 N acetic acid. The column was eluted with 2 N acetic acid and 8.2 ml. fractions collected. The column effluent was monitored at 254 nm. Fractions 46–51 were combined and lyophilized to yield 0.556 g. The product (0.556 g) was further purified by applying the material in a small volume of upper phase B:A:W, 4:1:5 (n-butanol:acetic acid:water) onto a column (2.5×100 cm) of Sephadex G-25 medium previously equilibrated with lower phase of the above system and then upper phase. The column was eluted with upper phase B:A:W and 4 ml. fractions collected. The effluent was monitored as above. Tubes 46–56 were shown to be homogeneous by thin layer chromatography systems 4:1:5; Rf=0.46 and 7:7:6 (isoamyl alcohol:pyridine:water); Rf=0.78 on silica gel. Thin layer chromatograms were visualized with ninhydrin and chlorine peptide reagent.

Amino acid analysis following methane sulfonic acid hydrolysis gave the following ratios: Gly 0.99; Tyr 1.01; Phe 1.00; Ala 0.97; $NH_3$ 1.00.

EXAMPLE 3

L-Tyrosyl-D-Ala-glycyl-L-phenylalanyl-2-MeAla-OH

Chloromethylated polystyrene resin is esterified with Boc-2-MeAla-OH according to the procedure of Gisin, *Helv. Chim. Acta.*, 56, 1976 (1973) and the polymeric ester is treated according to the procedure of example 1 for incorporation of Boc-Phe-OH, Boc-Gly-OH, Boc-D-Ala-OH and Boc-Tyr(Bzl)-OH. The resulting peptido resin is treated according to the procedure of example 2 to yield the title pentapeptidic acid.

EXAMPLE 4

L-Tyrosyl-D-Ala-glycyl-L-phenylalanyl-2-MeAla-ethylamide

Treatment of the peptido resin of example 3 with ethylamine in a sealed flask for 10 hours followed by removal of excess ethylamine, extraction with DMF filtration and evaporation of the filtrate yields the title ethylamide.

EXAMPLE 5

L-tyrosyl-D-Met-glycyl-L-phenylalanyl-2-MeAla-amide

The procedure of example 1 is repeated, with the exception that the fourth amino acid introduced into the solid phase reactor is Boc-D-Met-OH. The peptido resin is cleaved and worked up in accordance with the procedure of example 2 to yield the title compound.

EXAMPLE 6

L-tyrosyl-D-seryl-glycyl-L-phenylalanyl-2-MeAla-amide

The procedure of example 1 is repeated, with the exception that the fourth amino acid introduced into the solid phase reactor is t-Boc-O-Bzl-D-Ser-OH. The peptido resin is cleaved and worked up in accordance with the procedure of example 2 to yield the title compound.

What is claimed is:
1. A polypeptide of the formula:

L-Tyr-D-X-Gly-L-Phe-2-MeAla-R in which

X is alanyl or methionyl;
and
R is —OH, —NH$_2$ or —NHC$_n$H$_{2n+1}$ where n is 1, 2, 3 or 4 or a pharmaceutically acceptable salt thereof.

2. A compound of claim 1 of the formula:

L-Tyr-D-Ala-Gly-L-Phe-2-MeAla-R where R is —NH$_2$ or —NHC$_n$H$_{2n+1}$, and n is 1, 2, 3 or 4, or a pharmaceutically acceptable acid addition salt thereof.

3. The compound of claim 1 which is L-Tyr-D-Ala-Gly-L-Phe-2-MeAla-NH$_2$ or a pharmaceutically acceptable salt thereof.

4. The compound of claim 1 which is L-Tyr-D-Ala-Gly-L-Phe-2-MeAla-OH or a pharmaceutically acceptable salt thereof.

5. The compound of claim 1 which is L-Tyr-D-Ala-Gly-L-Phe-2-MeAla-NHC$_2$H$_5$ or a pharmaceutically acceptable salt thereof.

6. The compound of claim 1 which is L-Tyr-D-Met-Gly-L-Phe-2-MeAla-NH$_2$ or a pharmaceutically acceptable salt thereof.

* * * * *